(12) United States Patent
Lizio et al.

(10) Patent No.: US 8,431,157 B2
(45) Date of Patent: Apr. 30, 2013

(54) PARTLY NEUTRALISED ANIONIC (METH) ACRYLATE COPOLYMER

(75) Inventors: Rosario Lizio, Rossdorf (DE); Hans-Ulrich Petereit, Darmstadt (DE); Erna Roth, Darmstadt (DE); Michael Damm, Roedermark (DE); Ruediger Alexowsky, Nauheim (DE)

(73) Assignee: Evonik Roehm GmbH, Darmstadt (DE)

( * ) Notice: Subject to any disclaimer, the term of this patent is extended or adjusted under 35 U.S.C. 154(b) by 1128 days.

(21) Appl. No.: 11/815,632

(22) PCT Filed: Dec. 15, 2005

(86) PCT No.: PCT/EP2005/013513
§ 371 (c)(1), (2), (4) Date: Aug. 6, 2007

(87) PCT Pub. No.: WO2006/087027
PCT Pub. Date: Aug. 24, 2006

(65) Prior Publication Data
US 2009/0041842 A1    Feb. 12, 2009

(30) Foreign Application Priority Data
Feb. 15, 2005  (DE) .......................... 10 2005 007 059

(51) Int. Cl.
*A61K 9/16* (2006.01)
*A61K 9/20* (2006.01)

(52) U.S. Cl.
USPC .......................................... 424/475; 424/497

(58) Field of Classification Search .................. None
See application file for complete search history.

(56) References Cited

U.S. PATENT DOCUMENTS

| | | | | |
|---|---|---|---|---|
| 4,520,172 A | * | 5/1985 | Lehmann et al. | 525/369 |
| 5,523,222 A | * | 6/1996 | Page et al. | 800/25 |
| 5,648,399 A | * | 7/1997 | Friedman et al. | 514/772.6 |
| 5,753,215 A | * | 5/1998 | Mougin et al. | 424/70.11 |
| 5,958,458 A | * | 9/1999 | Norling et al. | 424/490 |
| 2003/0054038 A1 | * | 3/2003 | Crew et al. | 424/486 |
| 2006/0269605 A1 | | 11/2006 | Lizio et al. | |
| 2007/0026082 A1 | | 2/2007 | Lizio et al. | |
| 2007/0042045 A1 | | 2/2007 | Lizio et al. | |
| 2008/0044470 A1 | | 2/2008 | Petereit et al. | |
| 2008/0166416 A1 | | 7/2008 | Lizio et al. | |

FOREIGN PATENT DOCUMENTS

| | | | |
|---|---|---|---|
| CA | 2532487 | * | 7/2004 |
| EP | 0 088 951 | | 9/1983 |
| EP | 0 404 558 A1 | | 12/1990 |
| JP | 58-167521 | | 10/1983 |
| JP | 3-128316 | | 5/1991 |
| WO | WO 2005065726 | * | 7/2005 |

OTHER PUBLICATIONS

U.S. Appl. No. 60/908,855, filed Mar. 29, 2007, Lizio, et al.
U.S. Appl. No. 11/780,915, filed Jul. 20, 2007, Lizio, et al.
U.S. Appl. No. 11/994,440, filed Jan. 2, 2008, Peterfeit, et al.
U.S. Appl. No. 11/815,677, filed Aug. 7, 2007, Petereit, et al.
U.S. Appl. No. 11/816,372, filed Aug. 15, 2007, Petereit, et al.
U.S. Appl. No. 11/721,399, filed Jun. 11, 2007, Lizio, et al.
U.S. Appl. No. 12/598,138, filed Oct. 29, 2009, Liu, et al.

* cited by examiner

*Primary Examiner* — David J Blanchard
*Assistant Examiner* — Thurman Wheeler
(74) *Attorney, Agent, or Firm* — Oblon, Spivak, McClelland, Maier & Neustadt, L.L.P.

(57) ABSTRACT

The invention relates to a partly neutralized anionic (meth) acrylate copolymer consisting of radically polymerized units containing 25-95% by weight (meth)acrylic acid $C_1$ to $C_4$ alkylesters and 5-75% by weight (meth)acrylate monomer with an anionic group, wherein 0.1 to 25% contained anionic groups are neutralized by a base. Said invention is characterized in that said base is embodied in the form of an cationic organic base whose molecular weight is greater than 150. A medical form containing said partly neutralized anionic (meth)acrylate copolymer and the use of said partly neutralized anionic (meth)acrylate copolymer for producing a medical form rapidly releasing an active substance having a determined pH value are also disclosed.

16 Claims, No Drawings

PARTLY NEUTRALISED ANIONIC (METH) ACRYLATE COPOLYMER

The invention relates to a partially neutralized anionic (meth)acrylate copolymer, to a pharmaceutical form coated therewith, to process for producing the pharmaceutical form and to the use of the partially neutralized (meth)acrylate copolymer for producing a pharmaceutical form which releases the active ingredient rapidly at a particular pH.

PRIOR ART

EP 0 088 951 A2 describes a process for coating pharmaceutical forms by means of a coating agent dispersed in water. Partial neutralization of the carboxyl groups is recommended for redispersion of carboxyl group-containing (meth)acrylate copolymers from powders to dispersions. Salt formation of the acidic groups takes place by reaction with a base. Suitable bases are alkalis such as, for example, sodium hydroxide solution, potassium hydroxide solution, sodium carbonate, potassium carbonate, sodium bicarbonate, trisodium phosphate, trisodium citrate or ammonia or physiologically tolerated amines such as triethanolamine or tris(hydroxymethyl)aminomethane. A degree of neutralization of from 0.1 to 10% by weight of the carboxyl groups present in the copolymer is favourable in relation to the redispersion.

WO 2004/096185 describes a pharmaceutical form and a process for its production. The pharmaceutical form is coated with an anionic (meth)acrylate copolymer which may be partially neutralized if required. In order to prepare a solution of the anionic copolymer it is normally necessary for the acidic groups to be partially or completely neutralized.

The anionic copolymer may for example be stirred gradually in a final concentration of from 1 to 40% by weight into water and, during this, be partially or completely neutralized by adding a basic substance such as, for example, NaOH, KOH, ammonium hydroxide or organic bases such as, for example, triethanolamine. It is also possible to employ a powder of the copolymer, to which a base, e.g. NaOH, has already been added during its preparation for the purpose of (partial) neutralization, so that the powder is already a (partially) neutralized polymer. The pH of the solution is normally above 4, e.g. in the range from 4 to about 7.

PROBLEM AND SOLUTION

Anionic (meth)acrylate copolymers, e.g. of the EUDRAGIT® L, EUDRAGIT® L 100-55, EUDRAGIT® S or EUDRAGIT® FS type, are known as coatings which are soluble in intestinal juice for pharmaceutical forms. Depending on the monomer composition, but especially depending on the content of anionic groups, the anionic (meth)acrylate copolymers are characterized by specific pH values for dissolution in intestinal juice or in simulated intestinal fluid. Depending on the polymer type, the specific pH values for dissolution, or the pH values for the specific start of dissolution, are in the range of for example pH 5.5 to 7.5. At and above the specific pH for dissolution of the respective anionic (meth)acrylate copolymer, pharmaceutical forms coated therewith release the contained active ingredient. The specific pH values for dissolution thus characterize the start of the release of active ingredient.

It is known to employ anionic (meth)acrylate copolymers in partially neutralized form. An improved solubility of the polymer in water and a stabilization of the polymer dispersions is achieved thereby. Bases recommended for the partial neutralization are normally substances such as NaOH, KOH, ammonium hydroxide or organic bases such as, for example, triethanolamine.

Comparison of films of anionic (meth)acrylate copolymers which have been partially neutralized for example by means of NaOH, and which have not been partially neutralized, reveals that the partially neutralized films dissolve more rapidly in a buffer system at their specific pH for dissolution than the non-neutralized films.

The same applies to the use of a partially neutralized anionic (meth)acrylate copolymer as coating agent for a pharmaceutical form which releases the contained active ingredient in the USP 28 release test at the specific pH of the start of release of active ingredient more rapidly than a comparable pharmaceutical form with the same polymer pulling but without partial neutralization.

Pharmaceutical forms which would show such an accelerated active ingredient release behaviour which has its onset at the pH specific for the (meth)acrylate copolymer employed would be desirable for a number of therapies. However, the inventors have established that the behaviour described above for partially neutralized films and for pharmaceutical forms coated with partially neutralized films is not operative or is operative to only a reduced extent if the bases known from the state of the art have been used for the partial neutralization, and the films or pharmaceutical forms are initially left at pH 1.2 for two hours before buffering to the specific pH for the start of active ingredient release. However, these are precisely the conditions present in vivo when a pharmaceutical form initially reaches the stomach and only then is transported into the intestinal tract. The known partial neutralization of anionic (meth)acrylate copolymers is therefore unsuitable for achieving an accelerated active ingredient release behaviour.

An object was therefore regarded as being to formulate anionic (meth)acrylate copolymers in such a way that pharmaceutical forms coated therewith release the contained active ingredient in accelerated fashion at and above the specific pH for dissolution.

The object is achieved by a partially neutralized anionic (meth)acrylate copolymer consisting of free-radical polymerized units of 25 to 95% by weight $C_1$- to $C_4$-alkyl esters of acrylic or of methacrylic acid and 5 to 75% by weight (meth)acrylate monomers having an anionic group, where 0.1 to 25% of the contained anionic groups are neutralized by a base, characterized in that the base is lysine or a cationic, organic base having a molecular weight above 150.

MODE OF OPERATION OF THE INVENTION

Anionic (meth)acrylate Copolymer

The invention relates to a partially neutralized anionic (meth)acrylate copolymer.

The anionic (meth)acrylate copolymer comprises 25 to 95, preferably 40 to 95, in particular 60 to 40, % by weight free-radical polymerized $C_1$- to $C_4$-alkyl esters of acrylic or of methacrylic acid and 75 to 5, preferably 60 to 5, in particular 40 to 60, % by weight (meth)acrylate monomers having an anionic group.

The proportions mentioned normally add up to 100% by weight. However it is also possible in addition, without this leading to an impairment or alteration of the essential properties, for small amounts in the region of 0 to 10, for example 1 to 5, % by weight of further monomers capable of vinylic copolymerization, such as, for example, hydroxyethyl methacrylate or hydroxyethyl acrylate, to be present. It is preferred for no further monomers capable of vinylic copolymerization to be present.

C₁- to C₄-alkyl esters of acrylic or methacrylic acid are in particular methyl methacrylate, ethyl methacrylate, butyl methacrylate, methyl acrylate, ethyl acrylate and butyl acrylate.

A (meth)acrylate monomer having an anionic group is, for example, acrylic acid, with preference for methacrylic acid.

Suitable anionic (meth)acrylate copolymers are those composed of 40 to 60% by weight methacrylic acid and 60 to 40% by weight methyl methacrylate or 60 to 40% by weight ethyl acrylate (EUDRAGIT® L or EUDRAGIT® L 100-55 types).

EUDRAGIT® L is a copolymer of 50% by weight methyl methacrylate and 50% by weight methacrylic acid. The pH of the start of the specific active ingredient release in intestinal juice or simulated intestinal fluid can be stated to be pH 6.0.

EUDRAGIT® L 100-55 is a copolymer of 50% by weight ethyl acrylate and 50% by weight methacrylic acid. EUDRAGIT® L 30 D-55 is a dispersion comprising 30% by weight EUDRAGIT® L 100-55. The pH of the start of the specific active ingredient release in intestinal juice or simulated intestinal fluid can be stated to be pH 5.5.

Likewise suitable are anionic (meth)acrylate copolymers composed of 20 to 40% by weight methacrylic acid and 80 to 60% by weight methyl methacrylate (EUDRAGIT® S type). The pH of the start of the specific active ingredient release in intestinal juice or simulated intestinal fluid can be stated to be pH 7.0.

Suitable (meth)acrylate copolymers are those consisting of 10 to 30% by weight methyl methacrylate, 50 to 70% by weight methyl acrylate and 5 to 15% by weight methacrylic acid (EUDRAGIT® FS type). The pH at the start of the specific active ingredient release in intestinal juice or simulated intestinal fluid can be stated to be pH 7.0.

EUDRAGIT® FS is a copolymer of 25% by weight methyl methacrylate, 65% by weight methyl acrylate and 10% by weight methacrylic acid. EUDRAGIT® FS 30 D is a dispersion comprising 30% by weight EUDRAGIT® FS.

Additionally suitable is a copolymer composed of
20 to 34% by weight methacrylic acid and/or acrylic acid,
20 to 69% by weight methyl acrylate and
0 to 40% by weight ethyl acrylate and/or where appropriate
0 to 10% by weight further monomers capable of vinylic copolymerization,
with the proviso that the glass transition temperature of the copolymer according to ISO 11357-2, subsection 3.3.3, is not more than 60° C. This (meth)acrylate copolymer is particularly suitable, because of its good elongation at break properties, for compressing pellets to tablets.

Additionally suitable are copolymers composed of
20 to 33% by weight methacrylic acid and/or acrylic acid,
5 to 30% by weight methyl acrylate and
20 to 40% by weight ethyl acrylate and
more than 10 to 30% by weight butyl methacrylate and where appropriate
0 to 10% by weight further monomers capable of vinylic copolymerization,
where the proportions of the monomers add up to 100% by weight,
with the proviso that the glass transition temperature of the copolymer according to ISO 11357-2, subsection 3.3.3 (midpoint temperature $T_{mg}$), is 55 to 70° C. Copolymers of this type are particularly suitable, because of its good mechanical properties, for compressing pellets to tablets.

The abovementioned copolymer is composed in particular of free-radical polymerized units of
20 to 33, preferably 25 to 32, particularly preferably 28 to 31% by weight methacrylic acid or acrylic acid, with preference for methacrylic acid,
5 to 30, preferably 10 to 28, particularly preferably 15 to 25% by weight methyl acrylate,
20 to 40, preferably 25 to 35, particularly preferably 18 to 22% by weight ethyl acrylate, and
more than 10 to 30, preferably 15 to 25, particularly preferably 18 to 22% by weight butyl methacrylate,
where the monomer composition is chosen so that the glass transition temperature of the copolymer is from 55 to 70° C., preferably 59 to 66, particularly preferably 60 to 65° C.

Glass transition temperature means in this connection in particular the midpoint temperature $T_{mg}$ according to ISO 11357-2, subsection 3.3.3. Measurement takes place without added plasticizer, with residual monomer contents (REMO) of less than 100 ppm, with a heating rate of 10° C./min and under a nitrogen atmosphere.

The copolymer preferably consists essentially to exclusively of 90, 95 or 99 to 100% by weight of the monomers methacrylic acid, methyl acrylate, ethyl acrylate and butyl methacrylate in the ranges of amounts indicated above.

However, it is possible, without this necessarily leading to an impairment of the essential properties, for small amounts in the range from 0 to 10, e.g. 1 to 5% by weight of further monomers capable of vinylic copolymerization additionally to be present, such as, for example, methyl methacrylate, butyl acrylate, hydroxyethyl methacrylate, vinylpyrrolidone, vinylmalonic acid, styrene, vinyl alcohol, vinyl acetate and/or derivatives thereof.

Preparation of the Anionic (meth)acrylate Copolymers

The anionic (meth)acrylate copolymers can be prepared in a manner known per se by free-radical polymerization of the monomers (see, for example, EP 0 704 207 A2 and EP 0 704 208 A2). The copolymer according to the invention can be prepared in a manner known per se by free-radical emulsion polymerization in aqueous phase in the presence of, preferably, anionic emulsifiers, for example by the process described in DE-C 2 135 073.

The copolymer can be prepared by conventional processes of free-radical polymerization continuously or discontinuously (batch processes) in the presence of free-radical forming initiators and, where appropriate, regulators to adjust the molecular weight undiluted, in solution, by bead polymerization or in emulsion. The average molecular weight Mw (weight average, determined for example by measuring the solution viscosity) may be for example in the range from 80,000 to 1,000,000 (g/mol). Emulsion polymerization in aqueous phase in the presence of water-soluble initiators and (preferably anionic) emulsifiers is preferred.

In the case of bulk polymerization, the copolymer can be obtained in solid form by crushing, extrusion, granulation or hot cut.

The (meth)acrylate copolymers are obtained in a manner known per se by free-radical bulk, solution, bead or emulsion polymerization. They must before processing be brought to the particle size range of the invention by suitable grinding, drying or spraying processes. This can take place by simple crushing of extruded and cooled pellets or hot cut.

The use of powders may be advantageous especially on mixture with other powders or liquids. Suitable apparatuses for producing powders are familiar to the skilled person, e.g. air jet mills, pinned disc mills, compartment mills. It is possible where appropriate to include appropriate sieving steps. A suitable mill for industrial large quantities is, for example, an opposed jet mill (Multi No. 4200) operated with a gauge pressure of about 6 bar.

Partial Neutralization

Suitable cationic, organic bases having an $M_w$ of >150, preferably >155, particularly preferably >160, e.g. from >150 to 20,000 are:

The cationic, basic amino acids histidine and/or arginine. The amino acids glutamine and asparagine are unsuitable because they have a non-protonated amide function and are thus not to be included among cationic bases.

Natural or synthetic oligomers or polymers, e.g. composed of 3 to 100, preferably 5 to 25, units, of histidine, arginine or lysine, polyhistidines, polyarginines, polylysines, cationic or zwitterionic phospholipids such as, for example, phosphatidylcholine, ribonucleosides: products of the condensation of the hydroxyl function on carbon atom 1 of the ribose with the heterocyclic amino function of the bases adenine, guanine, cytosine, thymine or uracil, according to the occurrence in the RNA deoxyribonucleosides: products of the condensation of the hydroxyl function on carbon atom 1 of the deoxyribose with the heterocyclic amino function of the bases adenine, guanine, cytosine, thymine or uracil, according to the occurrence in the DNA.

Bases from cationic surface-active excipients or emulsifiers such as benzalkonium (CAS RN: 8001-54-5), benzethonium (CAS 121-54-0), cetalkonium (CAS 122-18-9), cetrimide (CAS 8044-71-1), cetrimonium (CAS 57-09-0), cetylpyridinium (CAS 123-03-5), stearalkonium (CAS 122-19-0), diallyldimethylammonium (CAS 230-993-8).

Bases unsuitable for the purposes of the invention are those expressly mentioned in EP 0 088 951 A2 or WO 2004/096185 or derivable therefrom. The following are excluded in particular: sodium hydroxide solution, potassium hydroxide solution (KOH), ammonium hydroxide or organic bases such as, for example, triethanolamine, sodium carbonate, potassium carbonate, sodium bicarbonate, trisodium phosphate, trisodium citrate or ammonia or physiologically tolerated amines such as triethanolamine or tris(hydroxymethyl)aminomethane.

These bases have an Mw not exceeding 150 (triethanolamine). Although triethanolamine is close with its molecular weight to the amino acids histidine, arginine, lysine, the effect according to the invention occurs only inadequately or not at all with this substance. Trisodium phosphate, trisodium citrate are not cationic in nature but are salts of the corresponding acids. Ammonium hydroxide, sodium hydroxide solution, potassium hydroxide solution (KOH), sodium carbonate, potassium carbonate, sodium bicarbonate have only low molecular weights or are to be included among the inorganic bases.

The molecular weight of the substances mentioned is known or can be calculated on the basis of the atomic weights of the atoms present in the molecule.

Adjustment of the Degree of Partial Neutralization by Mixtures

Mixtures may also result in technical advantages in the adjustment of the degree of partial neutralization. The invention relates to mixtures of anionic (meth)acrylate copolymers differing in the degree of partial neutralization, consisting of free-radical polymerized units of 25 to 95% by weight $C_1$- to $C_4$-alkyl esters of acrylic or of methacrylic acid and 5 to 75% by weight (meth)acrylate monomers having an anionic group, characterized in that 0.1 to 25% of the contained anionic groups, as calculated average for the mixture, are neutralized by a base which is lysine or a cationic, organic base having a molecular weight above 150. It is possible for example to mix an anionic (meth)acrylate copolymer which is not partially neutralized and consists of free-radical polymerized units of 25 to 95% by weight $C_1$-to $C_4$-alkyl esters of acrylic or of methacrylic acid and 5 to 75% by weight (meth)acrylate monomers having an anionic group with a partially neutralized (meth)acrylate copolymer of the same monomer composition within the stated quantitative ranges so that 0.1 to 25% of the contained anionic groups, as calculated average for the mixture, are neutralized. The mixture can be prepared for example by stirring a powder which has been obtained from a dispersion of a partially neutralized, anionic (meth)acrylate copolymer, e.g. by spray drying or freeze drying, into a dispersion of an anionic (meth)acrylate copolymer which has not been partially neutralized.

The cationic, organic base having a molecular weight above 150 is, following the principle of the present invention, again for example histidine, arginine, lysine, a polyhistidine, a polyarginine, a polylysine, a phospholipid such as phosphatidylcholine, a ribonucleoside or a deoxyribonucleoside, a base from cationic surface-active excipients or emulsifiers.

Mixtures

The (meth)acrylate copolymer which has been partially neutralized according to the invention is further suitable for mixing with other pharmaceutically utilized copolymers in order to modify the properties thereof. This increases the scope for configuration by the skilled person when adjusting specifically modified release profiles. The invention accordingly relates to a partially neutralized (meth)acrylate copolymer, characterized in that it is present in a mixture with copolymers of methyl methacrylate and/or ethyl acrylate and where appropriate less than 5% by weight methacrylic acid, copolymers of methyl methacrylate, butyl methacrylate and dimethylethyl methacrylate, copolymers of methyl methacrylate, ethyl acrylate and trimethylammoniumethyl methacrylate, copolymers of methyl methacrylate and ethyl acrylate, polyvinylpyrrolidones (PVP), polyvinyl alcohols, polyvinyl alcohol-polyethylene glycol graft copolymers (Kollicoat®), starch and its derivatives, polyvinyl acetate phthalate (PVAP, Coateric®), polyvinyl acetate (PVAc, Kollicoat), vinyl acetate-vinylpyrrolidone copolymer (Kollidon® VA64), vinyl acetate: crotonic acid 9:1 copolymer (VAC:CRA, Kollicoat® VAC), polyethylene glycols having a molecular weight above 1000 (g/mol), chitosan, a crosslinked and/or noncrosslinked polyacrylic acid, an Na alginate, and/or a pectin.

Dispersions

The partially neutralized (meth)acrylate copolymer may be for example in the form of an aqueous dispersion with a solids content of from 10 to 50 percent.

The partially neutralized (meth)acrylate copolymer may be in the form of a redispersible powder which has been obtained from a dispersion for example by spray drying.

Dispersions/partial Neutralization

The emulsion polymer is preferably produced and used in the form of a 10 to 50 percent by weight, in particular 20 to 40%, aqueous dispersion. A solids content of 30% by weight is preferred as commercial form. Partial neutralization of the methacrylic acid units can be dispensed with for processing; it is, however, possible, for example to an extent of up to 5 or 10 mol %, if a stabilization or thickening of the coating agent dispersion is desirable. The weight-average size (radius) of the latex particles is normally 40 to 100 nm, preferably 50 to 70 nm, thus ensuring a viscosity below 1000 mPa·s which is favourable for processing techniques. The particle size can be determined by laser diffraction, e.g. using the Mastersizer 2000 (from Malvern).

With higher degrees of neutralization, e.g. 10 to 50 mol %, or complete neutralization it is possible to convert the copolymer into a dissolved state.

In order to prepare a solution of the anionic copolymer it is normally necessary for the acidic groups to be partially or completely neutralized. The anionic copolymer may for example be stirred gradually in a final concentration of from 1 to 40% by weight into water and, during this, be partially or completely neutralized by adding a basic substance according to the invention such as, for example, lysine or arginine. It is also possible to employ a powder of the copolymer, to which a base, e.g. lysine, has already been added during its preparation for the purpose of (partial) neutralization, so that the powder is already a (partially) neutralized polymer. The pH of the solution is normally above 4, e.g. in the range from 4 to about 7. It is also possible in this connection for batches of completely or partially neutralized dispersions to be mixed for example with non-neutralized dispersions and further processed in the manner described, i.e. use the mixture for coatings or initially freeze dry or spray dry to give a powder.

The dispersion may also for example be spray dried or freeze dried in a manner known per se and be provided in the form of a redispersible powder (see, for example, EP-A 0 262 326). Alternative processes are freeze drying or coagulation and squeezing out the water in an extruder with subsequent granulation (see, for example, EP-A 0 683 028).

Copolymer dispersions of spray-dried or freeze-dried and redispersed powders may exhibit an increased shear stability. This is advantageous in particular for spray application. This advantage is strongly evident in particular when the copolymer present in the dispersion is partially neutralized to the extent of 2 to 10, preferably 5 to 7, mol % (based on the acidic groups present in the copolymer). It is preferred to add lysine or arginine for the partial neutralization for this purpose. An anionic emulsifier is preferably present in an amount of 0.1 to 2% by weight. Sodium lauryl sulphate is particularly preferred as emulsifier.

Use of the Partially Neutralized (meth)acrylate Copolymers

The partially neutralized anionic (meth)acrylate copolymer can be used as coating agent for a pharmaceutical form which, in the USP 28 release test for 2 hours at pH 1.2 and a subsequent change in the buffer to the pH of the start of active ingredient release, releases 90%, preferably 95 or 100% of the contained active ingredient in not more than 90%, preferably not more than 75%, in particular not more than 50% of the time which elapses therefor with a comparable pharmaceutical form with the same polymer pulling but without or partial neutralization by means of other bases not according to the invention.

If the pharmaceutical form not according to the invention releases in the USP 28 release test for 2 hours at pH 1.2 and a subsequent change in the buffer to the pH of the start of active ingredient release, e.g. pH 5.5, 90% of the active ingredient in, for example, 120 min, a comparable pharmaceutical form according to the invention requires not more than 108 min (90% of the time), not more than 90 min (75%) or not more than 60 min (50%) therefor.

The USP 28 release test, in particular by USP 28 <711> paddle method (=Apparatus 2), is sufficiently well known to the skilled person.

The typical test procedure is as follows:
1. The vessels of the release apparatus are each charged with 360 ml of 0.1M-HCl (pH 1.2) and the temperature of the waterbath is adjusted to 37±0.5° C.
2. The paddle stirrer is switched on with a rotation rate of 100 rpm.
3. 1 g of pellets is put into each vessel of the apparatus. Care is taken that there are no air bubbles on the pellet surface.
4. After 120 min, 140 ml of phosphate buffer solution (equilibrated at 37° C.), are added so that the desired pH results in the final volume of 500 ml: pH 5.5; 5.6; 5.7; 5.8 or 7.0.
5. Determination of the time for 100% active ingredient release, depending on the active ingredient, e.g. by photometry at 271 nm in the case of theophylline, in the circulating method.

Pharmaceutical Form

The invention relates to a pharmaceutical form comprising a core having an active pharmaceutical ingredient and comprising a polymer coating of a partially neutralized (meth) acrylate copolymer.

The pharmaceutical form may preferably comprise a polymer coating with lysine or arginine as neutralizing agent in combination with 5 to 25% by weight of a plasticizer.

The corresponding pharmaceutical form may be for example in the form of a multiparticulate pharmaceutical form, pellet-containing tablets, minitablets, capsules, sachets, effervescent tablets or reconstitutable powders.

Separating Layers

The pharmaceutical form may preferably have a layer comprising where appropriate a binder and lysine or a cationic, organic base having a molecular weight above 150 between the active ingredient-containing core and the polymer coating. The advantage of this in individual cases is that through the surface of the pharmaceutical form the active ingredient delivered base is replenished again from the inside. It is possible with this structure for active ingredient release to be speeded up further.

The pharmaceutical form may have a separating layer between the core having an active pharmaceutical ingredient and the polymer coating. The separating layer may advantageously serve the purpose of preventing interactions between ingredients of the core and of the polymer coating. The separating layer may consist of inert film formers (e.g. HPMC, HPC or (meth)acrylic acid copolymers) or for example talc or other suitable pharmaceutical substances. It is likewise possible to use combinations of film formers and talc or similar substances.

Process for Producing a Pharmaceutical Form

The invention further relates to a process for producing the pharmaceutical form according to the invention in a manner known per se by pharmaceutically customary processes such as direct compression, compression of dry, wet or sintered granules, extrusion and subsequent rounding off, wet or dry granulation or direct pelleting or by binding powders (powder layering) onto active ingredient-free beads or neutral cores (nonpareilles) or active ingredient-containing particles and by applying the polymer coating in a spray process or by fluidized bed granulation.

Production of Multiparticulate Pharmaceutical Forms

The invention is suitable in particular for producing multiparticulate pharmaceutical forms, because the copolymer according to the invention withstands the high pressures in the compression of the pellets with the filler.

The production of multiparticulate pharmaceutical forms by compression of a pharmaceutically usual binder with active ingredient-containing particles is described in detail for example Beckert et al. (1996), "Compression of enteric-coated pellets to disintegrating tablets", *International Journal of Pharmaceutics* 143, pp. 13-23, and in WO 96/01624.

Active ingredient-containing pellets can be produced by applying active ingredient by means of a layering process. For this purpose, active ingredient is homogenized together with further excipients (release agent, where appropriate plasticizer) and dissolved or suspended in a binder. The liquid can be applied by means of a fluidized bed process to placebo pellets or other suitable carrier materials, with evaporation of the solvent or suspending agent (literature: *International Journal of Pharmaceutics* 143, pp. 13-23). The production process may be followed by a drying step. The active ingredient can be applied in a plurality of layers.

Some active ingredients, e.g. acetylsalicylic acid, are commercially available in the form of active ingredient crystals and can be employed in this form instead of active ingredient-containing pellets.

Film coatings on active ingredient-containing pellets are normally applied in fluidized bed apparatuses. Formulation examples are mentioned in this application. Film formers are normally mixed with plasticizers and release agents by a suitable process. It is possible in this case for the film formers to be in the form of a solution or suspension. The excipients for the film formation may likewise be dissolved or suspended. Organic or aqueous solvents or dispersants can be used.

It is additionally possible to use stabilizers to stabilize the dispersion (for example: Tween 80 or other suitable emulsifiers or stabilizers).

Examples of release agents are glycerol monostearate or other suitable fatty acid derivatives, silica derivatives or talc. Examples of plasticizers are propylene glycol, phthalates, polyethylene glycols, sebacates or citrates, and other substances mentioned in the literature.

It is possible to apply between active ingredient-containing and intestine-soluble copolymer layer a separating layer which serves to separate active ingredient and coating material for the purpose of preventing interactions. This layer may consist of inert film formers (e.g. HPMC, HPC or (meth) acrylic acid copolymers) or, for example, talc or other suitable pharmaceutical substances. It is likewise possible to use combinations of film formers and talc or similar substances.

It is also possible to apply a separating layer composed of partially or completely neutralized copolymer dispersions.

Mixtures for producing tablets from coated particles are prepared by mixing the pellets with suitable binders for tableting, if necessary adding disintegration-promoting substances and if necessary adding lubricants. The mixing can take place in suitable machines. Unsuitable mixers are those leading to damage to the coated particles, e.g. ploughshare mixers. A specific sequence of addition of the excipients to the coated particles may be necessary to achieve suitable short disintegration times. It is possible by premixing with the coated particles with the lubricant or mould release agent magnesium stearate for its surface to be rendered hydrophobic and thus for adhesion to be avoided.

Mixtures suitable for tableting normally comprise 3 to 15% by weight of a disintegration aid, e.g. Kollidon CL and, for example, 0.1 to 1% by weight of a lubricant and mould release agent such as magnesium stearate. The binder content is determined by the required proportion of coated particles.

Examples of typical binders are Cellactose®, microcrystalline cellulose, calcium phosphates, Ludipress®, lactose or other suitable sugars, calcium sulphates or starch derivatives. Substances of low apparent density are preferred.

Typical disintegration aids (disintegrants) are cross-linked starch or cellulose derivatives, and crosslinked polyvinylpyrrolidone. Cellulose derivatives are likewise suitable. The use of disintegration aids can be dispensed with through selection of a suitable binder.

Typical lubricants and mould release agents are magnesium stearates or other suitable salts of fatty acids or substances mentioned in the literature for this purpose (e.g. lauric acid, calcium stearate, talc, etc.). The use of a lubricant and mould release agent in the mixture can be dispensed with on use of suitable machines (e.g. tablet press with external lubrication), or suitable formulations.

A flow-improving aid can be added where appropriate to the mixture (e.g. colloidal silica derivatives, talc etc.).

The tableting can take place on conventional tablet presses, eccentric or rotary tablet presses, with compressive forces in the range from 5 to 40 kN, preferably 10-20 kN. The tablet presses may be equipped with systems for external lubrication. Special systems for die filling which avoid die filling by means of impeller paddles are employed where appropriate.

Further Processes for Producing the Pharmaceutical Form According to the Invention Application process takes place by spray application from organic solution or preferably aqueous dispersions by melting or by direct powder application. The crucial factor for the implementation in this case is that uniform, pore-free coatings result.

For prior art application processes see, for example, Bauer, Lehmann, Osterwald, Rothgang, "Überzogene Arzneiformen" Wissenschaftliche Verlagsgesellschaft mbH, Stuttgart, Chapter 7, pp. 165-196

Relevant properties, required tests and specifications for the application are listed in pharmacopoeias.

Details are to be found in the customary textbooks, for example:

Voigt, R. (1984): Lehrbuch der pharmazeutischen Technologie; Verlag Chemie Weinheim—Beerfield Beach/Fla.—Basle.

Sucker, H., Fuchs, P., Speiser, P.: Pharmazeutische Technologie, Georg Thieme Verlag Stuttgart (1991), especially Chapters 15 and 16, pp. 626-642.

Gennaro, A. R. (editor), Remington's Pharmaceutical Sciences, Mack Publishing Co., Easton Pa. (1985), Chapter 88, pp. 1567-1573.

List, P. H. (1982): Arzneiformenlehre, Wissen-schaftliche Verlagsgesellschaft mbH, Stuttgart.

EXAMPLES

USP 28 <711> Paddle Method (=Apparatus 2) Release Test for Theophylline Pellets

Procedure:

1. The vessels of the release apparatus are each charged with 360 ml of 0.1M-HCl (pH 1.2) and the temperature of the waterbath is adjusted to 37±0.5° C.
2. The paddle stirrer is switched on with a rotation rate of 100 rpm.
3. 1 g of pellets is put into each vessel of the apparatus. Care is taken that there are no air bubbles on the pellet surface.
4. After 120 min, 140 ml of phosphate buffer solution (equilibrated at 37° C.), are added so that the desired pH results in the final volume of 500 ml: pH 5.5; 5.6; 5.7; 5.8 or 7.0.
5. Determination of the time for 100 active ingredient release (by photometry at 271 nm, in the circulating method). See Table 1 for results.

TABLE 1

Theophylline pellets with 30% coating of a copolymer of 50% by weight ethyl acrylate and 50% by weight methacrylic acid (EUDRAGIT ® L 30 D-55), 90% active ingredient released [min], USP 28 paddle method.

| beforehand | Example 1 15% partial neutralization with lysine | | Example 2 15% partial neutralization with NaOH | | Example 3 No partial neutralization | |
|---|---|---|---|---|---|---|
| 2 h pH 1.2 | + | − | + | − | + | − |
| pH 5.5 | 45 | 40 | 90 | 45 | 120 | 120 |
| pH 5.6 | 30 | 28 | 50 | 30 | 60 | 60 |
| pH 5.7 | 20 | 19 | 30 | 20 | 50 | 50 |
| pH 5.8 | 18 | 17 | 20 | 18 | 30 | 30 |
| pH 7.0 | Immediate active ingredient release | | | | | |

Example 1

Formulation with Lysine

Pellet coatings with EUDRAGIT L 30 D 55 partially neutralized with lysine.

30% dry matter of a polymer dispersion (methacrylate copolymer of 50% by weight methacrylic acid and 50% by weight ethyl acrylate) with the following formulations are coated onto 100 g of theophylline pellets supplied by Klinge Pharma having a particle size of 0.7-1.0 mm. The total dry content application amounts to 35.7% by weight based on the batch quantity See Table 1 for release investigation 90% by weight of the active ingredient.

| Materials | (g) |
|---|---|
| EUDRAGIT L 30 D-55 | 100.00 |
| Lysine | 3.69 |
| Glycerol monostearate | 1.50 |
| Polysorbate 80 | 0.60 |
| Water dem. | 132.81 |
| Total | 238.60 |

Spray parameters in a Hüttlin Mycrolab:

| | |
|---|---|
| Spray nozzle | 0.6 mm |
| Spraying rate | 26 g/min/kg |
| Spraying pressure | 1.0 bar |
| Microclimate | 0.6 bar |
| Inlet airflow | 20 m³ |
| Inlet air temperature | 33-39° C. |
| Product temperature | 26-29° C. |
| Make-dry time in the apparatus | 10 min at 40° C. |
| Spraying time | 1.5-2 h |
| Drying overnight at | room temperature (RT) |

Example 2

Formulation with NaOH

Pellet coating with EUDRAGIT L 30 D 55 partially neutralized with NaOH.

30% dry matter of a polymer dispersion (methacrylate copolymer of 50% by weight methacrylic acid and 50% by weight ethyl acrylate) with the following formulations are coated onto 100 g of theophylline pellets supplied by Klinge Pharma having a particle size of 0.7-1.0 mm. The total dry content application amounts to 33.11% by weight based on the batch quantity See Table 1 for release investigation 90% by weight of the active ingredient.

| Materials | (g) |
|---|---|
| EUDRAGIT L 30 D-55 | 100.00 |
| NaOH | 1.01 |
| Glycerol monostearate | 1.50 |
| Polysorbate 80 | 0.60 |
| Water dem. | 117.62 |
| Total | 220.73 |

Spray parameters in a Hüttlin Mycrolab:

| | |
|---|---|
| Spray nozzle | 0.6 mm |
| Spraying rate | 27 g/min/kg |
| Spraying pressure | 1.0 bar |
| Microclimate | 0.6 bar |
| Inlet airflow | 20 m³ |
| Inlet air temperature | 33-40° C. |
| Product temperature | 26-30° C. |
| Make-dry time in the apparatus | 10 min at 40° C. |
| Spraying time | 1-1.5 h |
| Drying overnight at | RT |

Example 3

Formulation Without Partial Neutralization

Pellet coating with EUDRAGIT L 30 D 55 without partial neutralization

30% dry matter of a polymer dispersion (methacrylate copolymer of 50% by weight methacrylic acid and 50% by weight ethyl acrylate) with the following formulations are coated onto 100 g of theophylline pellets supplied by Klinge Pharma having a particle size of 0.7-1.0 mm. The total dry content application amounts to 32.111% by weight based on the batch quantity See Table 1 for release investigation 90% by weight of the active ingredient.

| Materials | (g) |
|---|---|
| EUDRAGIT L 30 D-55 | 100.00 |
| Glycerol monostearate | 1.50 |
| Polysorbate 80 | 0.60 |
| Water dem. | 136.83 |
| Total | 238.93 |

Spray parameters in MiniGlatt:

| | |
|---|---|
| Spray nozzle | 0.5 mm |
| Spraying rate | 1-2 g/min |
| Spraying pressure | 0.8 bar |
| Inlet air | 0.7 bar |
| Inlet air temperature | 35-37° C. |
| Product temperature | 32-33° C. |
| Make-dry time in the apparatus | 10 min at 40° C. |
| Spraying time | approx 2-3 h |
| Drying overnight at | RT |

The invention claimed is:

1. A pharmaceutical form comprising a core having an active pharmaceutical ingredient and a polymer coating of a partially neutralized anionic (meth)acrylate copolymer comprising free-radical polymerized units of 25 to 95% by weight C1- to C4-alkyl esters of acrylic or of methacrylic acid and 5 to 75% by weight (meth)acrylate monomers having an anionic group, where 0.1 to 25% of the contained anionic groups are neutralized by a base, wherein the base is lysine or a cationic, organic base having a molecular weight above 150 selected from the group consisting of histidine, arginine, a polyhistidine, a polyarginine, a polylysine, a phospholipid, a ribonucleoside, a deoxyribonucleoside, and a base from cationic surface active excipients or emulsifiers, wherein the coating, in the USP 28 release test for 2 hours at pH 1.2 followed by a change in the buffer to obtain a pH in the range of 5.5 to 7.5 at which active ingredient release starts, releases 90% of the contained active ingredient in not more than 90% of the time which elapses in the same release test for 2 hours at pH 1.2 followed by a change in the buffer to obtain the same pH at which active ingredient release starts with a comparable pharmaceutical form with the same active ingredient and partially neutralized anionic polymer but with partial neutralization by bases other than lysine or a cationic, organic base having a molecular weight above 150.

2. The pharmaceutical form according to claim 1, wherein the anionic (meth)acrylate copolymer comprises free-radical polymerized units of (1) 40 to 60% by weight methacrylic acid and (2) 60 to 40% by weight methyl methacrylate or 60 to 40% by weight ethyl acrylate.

3. The pharmaceutical form according to claim 1, wherein said copolymer is present in a mixture with a copolymer of methyl methacrylate and/or ethyl acrylate and less than 5% by weight methacrylic acid, a copolymer of methyl methacrylate, butyl methacrylate and dimethylethyl methacrylate, a copolymer of methyl methacrylate, ethyl acrylate and trimethylammoniumethyl methacrylate, a copolymer of methyl methacrylate and ethyl acrylate, a polyvinylpyrrolidone (PVP), a polyvinyl alcohol, a polyvinyl alcohol-polyethylene glycol graft copolymer, starch and its derivatives, polyvinyl acetate phthalate (PVAP), polyvinyl acetate (PVAc), vinyl acetate-vinylpyrrolidone copolymer, vinyl acetate: crotonic acid 9:1 copolymer (VAC:CRA), polyethylene glycols having a molecular weight above 1000 (g/mol), chitosan, a crosslinked and/or noncrosslinked polyacrylic acid, an Na alginate, and/or a pectin.

4. The pharmaceutical form according to claim 1, wherein the partially neutralized anionic (meth)acrylate copolymer is a mixture of anionic (meth)acrylate copolymers differing in the degree of partial neutralization, comprising free-radical polymerized units of 25 to 95% by weight $C_1$- to $C_4$-alkyl esters of acrylic or of methacrylic acid and 5 to 75% by weight (meth)acrylate monomers having an anionic group, and the neutralized 0.1 to 25% of the contained anionic groups is a calculated average for the mixture.

5. The pharmaceutical form according to claim 1, wherein the polymer coating comprises lysine or arginine as a neutralizing agent in combination with 5 to 25% by weight of a plasticizer.

6. The pharmaceutical form according to claim 1, wherein a layer comprising a binder and lysine or a cationic, organic base having a molecular weight above 150 is located between the active ingredient-containing core and the polymer coating.

7. The pharmaceutical form according to claim 1, characterized in that a separating layer is applied between the core having an active pharmaceutical ingredient and the polymer coating.

8. The pharmaceutical form according to claim 1, wherein the pharmaceutical form is in the form of a multiparticulate pharmaceutical form, pellet-containing tablets, minitablets, capsules, sachets, effervescent tablets or reconstitutable powders.

9. The pharmaceutical form according to claim 1, wherein the base is lysine or an organic base having a molecular weight above 150 selected from the group consisting of histidine, a polyhistidine, a polyarginine, a polylysine, a phospholipid, a ribonucleoside, a deoxyribonucleoside, and a base from cationic surface-active excipients or emulsifiers.

10. The pharmaceutical form according to claim 1, wherein the base is lysine.

11. The pharmaceutical form according to claim 1, wherein the base is an organic base having a molecular weight above 150 selected from the group consisting of histidine, a polyhistidine, a polyarginine, a polylysine, a phospholipid, a ribonucleoside, a deoxyribonucleoside, and a base from cationic surface-active excipients or emulsifiers.

12. The pharmaceutical form according to claim 1, wherein the base is selected from the group consisting of lysine, arginine, histidine, a polyhistidine, a polyarginine, a polylysine, phosphatidylcholine, a ribonucleoside, and a deoxyribonucleoside.

13. The pharmaceutical form according to claim 1, wherein the cationic, organic base is selected from the group consisting of polyhistidines, polyarginine, polylysines, phospholipids, ribonucleosides, and deoxyribonucleosides.

14. The pharmaceutical form according to claim 1, wherein the cationic, organic base is selected from the group consisting of natural or synthetic oligomers or polymers having 3 to 100 histidine units, having 3 to 100 arginine units, or having 3 to 100 lysine units.

15. The pharmaceutical form according to claim 1, wherein the coating, in the USP 28 release test for 2 hours at pH 1.2 followed by a change in the buffer to obtain a pH in the range of 5.5 to 7.5 at which active ingredient release starts, releases 90% of the contained active ingredient in not more than 75% of the time which elapses in the same release test for 2 hours at pH 1.2 followed by a change in the buffer to obtain the same pH at which active ingredient release starts with a comparable pharmaceutical form with the same active ingredient and partially neutralized anionic polymer but with partial neutralization by bases other than lysine or a cationic, organic base having a molecular weight above 150.

16. The pharmaceutical form according to claim 1, wherein the coating, in the USP 28 release test for 2 hours at pH 1.2 followed by a change in the buffer to obtain a pH in the range of 5.5 to 7.5 at which active ingredient release starts, releases 90% of the contained active ingredient in not more than 50% of the time which elapses in the same release test for 2 hours at pH 1.2 followed by a change in the buffer to obtain the same pH at which active ingredient release starts with a comparable pharmaceutical form with the same active ingredient and partially neutralized anionic polymer but with partial neutralization by bases other than lysine or a cationic, organic base having a molecular weight above 150.

* * * * *